(12) United States Patent
Schena

(10) Patent No.: US 10,779,711 B2
(45) Date of Patent: *Sep. 22, 2020

(54) CENTER ROBOTIC ARM WITH FIVE-BAR SPHERICAL LINKAGE FOR ENDOSCOPIC CAMERA

(71) Applicant: INTUITIVE SURGICAL OPERATIONS, INC., Sunnyvale, CA (US)

(72) Inventor: Bruce M. Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 15/912,566

(22) Filed: Mar. 6, 2018

(65) Prior Publication Data

US 2018/0192859 A1  Jul. 12, 2018

Related U.S. Application Data

(60) Division of application No. 13/915,564, filed on Jun. 11, 2013, now Pat. No. 9,907,458, which is a
(Continued)

(51) Int. Cl.
*A61B 34/00* (2016.01)
*A61B 1/04* (2006.01)
(Continued)

(52) U.S. Cl.
CPC ............ *A61B 1/04* (2013.01); *A61B 1/00149* (2013.01); *A61B 34/30* (2016.02); *A61B 34/37* (2016.02);
(Continued)

(58) Field of Classification Search
CPC ...................................................... A61B 34/00
See application file for complete search history.

(56) References Cited

U.S. PATENT DOCUMENTS

| 4,496,279 A | 1/1985 | Langer |
| 5,301,566 A | 4/1994 | Tahmasebi et al. |

(Continued)

FOREIGN PATENT DOCUMENTS

| EP | 0595291 A1 | 5/1994 |
| JP | S60167785 A | 8/1985 |

(Continued)

OTHER PUBLICATIONS

Applicant Initiated Interview Summary dated Oct. 27, 2011 for U.S. Appl. No. 11/623,292, filed Jan. 15, 2007.
(Continued)

*Primary Examiner* — Lynsey C Eiseman

(57) ABSTRACT

A robotic arm including a parallel spherical five-bar linkage with a remote center of spherical rotation. The robotic arm movably supports an endoscopic camera. Two outboard links are pivotally coupled together. At least one of the two outboard links supports the endoscopic camera. Two inboard links are respectively pivotally coupled to the two outboard links such that the two inboard links are able to cross over one another. The two inboard links moveably support the two outboard links. A ground link is pivotally coupled to the two inboard links. The ground link moveably supports the two inboard links.

13 Claims, 11 Drawing Sheets

Related U.S. Application Data continuation of application No. 11/623,311, filed on Jan. 15, 2007, now Pat. No. 8,469,945.

(60) Provisional application No. 60/786,491, filed on Mar. 28, 2006, provisional application No. 60/762,233, filed on Jan. 25, 2006.

(51) Int. Cl.
| | |
|---|---|
| *A61B 34/30* | (2016.01) |
| *A61B 34/37* | (2016.01) |
| *B25J 17/02* | (2006.01) |
| *B25J 18/00* | (2006.01) |
| *A61B 1/00* | (2006.01) |
| *A61B 90/00* | (2016.01) |

(52) U.S. Cl.
CPC ........... *A61B 34/70* (2016.02); *B25J 17/0258* (2013.01); *B25J 18/007* (2013.01); *A61B 90/361* (2016.02); *Y10T 74/20305* (2015.01)

(56) References Cited

U.S. PATENT DOCUMENTS

| | | | |
|---|---|---|---|
| 5,397,323 | A | 3/1995 | Taylor et al. |
| 5,399,951 | A | 3/1995 | Lavallee et al. |
| 5,582,617 | A | 12/1996 | Klieman et al. |
| 5,800,423 | A | 9/1998 | Jensen |
| 5,833,656 | A | 11/1998 | Smith et al. |
| 5,966,991 | A | 10/1999 | Gosselin et al. |
| 6,024,576 | A | 2/2000 | Bevirt et al. |
| 6,154,198 | A | 11/2000 | Rosenberg |
| 6,355,048 | B1 | 3/2002 | Hong et al. |
| 6,406,472 | B1 | 6/2002 | Jensen |
| 6,424,885 | B1 | 7/2002 | Niemeyer et al. |
| 6,684,129 | B2 | 1/2004 | Salisbury et al. |
| 6,903,721 | B2 | 6/2005 | Braun et al. |
| 6,946,812 | B1 | 9/2005 | Martin et al. |
| 7,108,688 | B2 | 9/2006 | Jensen |
| 8,142,420 | B2 | 3/2012 | Schena |
| 8,162,926 | B2 | 4/2012 | Schena |
| 8,167,872 | B2 | 5/2012 | Schena |
| 8,167,873 | B2 | 5/2012 | Schena |
| 8,469,945 | B2 | 6/2013 | Schena |
| 8,506,556 | B2 | 8/2013 | Schena |
| 9,907,458 | B2 | 3/2018 | Schena et al. |
| 2002/0082612 | A1 | 6/2002 | Moll et al. |
| 2004/0024385 | A1 | 2/2004 | Stuart |
| 2004/0024387 | A1 | 2/2004 | Payandeh et al. |
| 2005/0183532 | A1 | 8/2005 | Najafi et al. |
| 2006/0243085 | A1 | 11/2006 | Hannaford et al. |
| 2013/0255425 | A1 | 10/2013 | Schena |
| 2013/0338434 | A1 | 12/2013 | Schena et al. |

FOREIGN PATENT DOCUMENTS

| | | |
|---|---|---|
| JP | H06261911 A | 9/1994 |
| JP | H10512983 A | 12/1998 |
| WO | WO-199622591 A1 | 7/1996 |
| WO | WO-2007114975 A2 | 10/2007 |
| WO | WO-2007120952 A2 | 10/2007 |

OTHER PUBLICATIONS

Applicant Initiated Interview Summary dated Oct. 28, 2011 for U.S. Appl. No. 11/623,281, filed Jan. 15, 2007.
Applicant Initiated Interview Summary dated Oct. 28, 2011 for U.S. Appl. No. 11/623,310, filed Jan. 15, 2007.
Applicant Initiated Interview Summary dated Oct. 28, 2011 for U.S. Appl. No. 11/623,311, filed Jan. 15, 2007.
Applicant Initiated Interview Summary dated Oct. 31, 2011 for U.S. Appl. No. 11/623,305, filed Jan. 15, 2007.
Chinzei, Kiyoyuki et al., "MR Compatible Surgical Assist Robot: System Integration and Preliminary Feasibility Study," in Proceedings of Third International Conference on Medical Imaging and Computer Assisted Surgery (MICCAI), 2000, pp. 921-930, vol. 1935, Springer-Verlag.
Extended European Search Report for Application No. 16153176.9, dated Sep. 28, 2016, 10 pages.
Frisoli, Antonio et al., "Mechanical Design and Kinematic Optimization of a Novel Six-Degree-Of-Freedom Parallel Mechanism," PKM99 1st International Conference on Parallel Kinematic Machines, Milan(Italy), 1999,11 pages. Internet http://percro.sssup.it/~antony/research/desktop/6_dof.htm.
Grace, Kenneth Wayne, "Kinematic Design of an Ophthalmic Surgery Robot and Feature Extracting Bilateral Manipulation," Doctoral Dissertation, Northwestern University, 1995, 94 pages.
Hannaford, Blake et al. "Novel Control System for Robotic Devices via USB," 1 page (plus 1 page enlargement), Internet http://hawkeye1.net/Projects/BRL_FHD3.1_poster_final.pdf.
Hunter, Ian W. et al., "Ophthalmic microsurgical robot and associated virtual environment," Comput. Biol. Med, 1995, vol. 25, Issue 2, pp. 173-182, Pergamon.
Lai, Fuji et al., "Evaluating control modes for constrained robotic surgery," IEEE International Conferenceon on Robotics & Automation San Francisco, Apr. 2000, vol. 1, pp. 603-609, IEEE.
Lum, Mitchell, Jay, Hiroshi et al., "Hybrid Analysis of a Spherical Mechanism for a Minimally Invasive Surgical (MIS) Robot—Design Concepts for Multiple Optimizations," 2003, pp. 1-6, IOS Press.
Lum, Mitchell, Jay, Hiroshi et al., "Kinematic Optimization of a Spherical Mechanism for a Minimally Invasive Surgical Robot," IEEE International Conference on Robotics and Automation, 2004, pp. 829-834, vol. 1, IEEE.
Lum, Mitchell Jay Hiroshi, "Kinematic Optimization of a 2-DOF Spherical Mechanism for a Minimally Invasive Surgical Robot," Proc. IEEE Conf. Robotics and Automation, 2004, 69 Pages, IEEE.
Lum, Mitchell J.H. et al., "Multidisciplinary Approach for Developing a New Minimally Invasive Surgical Robotic System," The first IEEE / RAS-EMBS International Conference on Biomedical Robotics and Biomechatronics, 2006, pp. 841-846, IEEE.
Lum, Mitchell J.H. et al., "Optimization of a Spherical Mechanism for a Minimally Invasive Surgical Robot: Theoretical and Experimental Approaches," IEEE Transactions on Biomedical Engineering, 2006, vol. 53, No. 7, pp. 1440-1445, IEEE.
Lum, Mitchell, Quantitative Performance Assessment of Surgical Robot Systems: TeleRobotic FLS, University of Washington, 2008.
Nagy, Istvan et al. "The Endo[PA]R System for Minimally Invasive Robotic Surgery," Technische Universitat Munchen, Dec. 2003, pp. 1-22.
Non-Final Office Action dated Aug. 9, 2012 for U.S. Appl. No. 13/431,894, filed Mar. 27, 2012.
Partial European Search Report for Application No. 16153176.9, dated Jun. 16, 2016, 7 pages.
PCT/US07/60948 International Search Report, dated Mar. 28, 2008, 4 pages.
PCT/US07/60948 Written Opinion of the International Search Authority, dated Jul. 29, 2008, 8 pages.
PCT/US07/60950 International Search Report, dated Feb. 26, 2008, 4 pages.
PCT/US07/60950 Written Opinion of the International Search Authority, dated Jul. 29, 2008, 9 pages.
Rosen, Jacob et al., "Spherical Mechanism Analysis of a Surgical Robot for Minimally Invasive Surgery Analytical and Experimental Approaches," Studies in Health Technology and Informatics—Medicine Meets Virtual Reality (MMVR), 2005, vol. 111, pp. 422-428, IOS Press.
Taylor, Russell H. et al., "Medical Robotics in Computer-Integrated Surgery," IEEE Transactions on Robotics md Automation, 2003, pp. 765-781, vol. 19—No. 5, IEEE.
University of Washington, "Mini Robot Design for Military Telesurgery in the Battlefield—Braking [sic] the Size Barrier for Surgical Manipulators," BioRobotics Laboratory> Surgical Technology> Device, Internet http://brl.ee.washington.edu/Research_Active/Surgery/Project_07/Project_07.html.

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wang, Yuan-Fang et al., "Choreographed Scope Maneuvering in Robotically-Assisted Laparoscopy with Active Vision Guidance," Proceedings of the 3rd IEEE Workshop on Applications of Computer Vision, 1996, 6 Pages, IEEE.

Westwood, James.D., et al.,"Medicine Meets Virtual Reality 13 The Magical Next Becomes the Medical Now," 2005, pp. 1-13, IOS Press.

US 10,779,711 B2

CENTER ROBOTIC ARM WITH FIVE-BAR SPHERICAL LINKAGE FOR ENDOSCOPIC CAMERA

CROSS REFERENCE TO RELATED APPLICATIONS

This application is a division of application Ser. No. 13/915,564, filed Jun. 11, 2013, which is a continuation of application Ser. No. 11/623,311, filed Jan. 15, 2007, now U.S. Pat. No. 8,469,945, which claims the benefit pursuant to 35 U.S.C. 119(e) of U.S. Provisional Application No. 60/786,491, filed Mar. 28, 2006, and U.S. Provisional Application No. 60/762,233, filed Jan. 25, 2006, each of which is hereby incorporated by reference in its entirety.

FIELD OF INVENTION

The embodiments of the invention relate generally to robotic surgical systems. More particularly, the embodiments of the invention relate to linkage in robotic arms.

BACKGROUND

Minimally invasive surgery (MIS) provides surgical techniques for operating on a patient through small incisions using a camera and elongated surgical instruments introduced to an internal surgical site, often through trocar sleeves or cannulas. The surgical site often comprises a body cavity, such as the patient's abdomen. The body cavity may optionally be distended using a clear fluid such as an insufflation gas. In traditional minimally invasive surgery, the surgeon manipulates the tissues using end effectors of the elongated surgical instruments by actuating the instrument's handles while viewing the surgical site on a video monitor.

A common form of minimally invasive surgery is endoscopy. Laparoscopy is a type of endoscopy for performing minimally invasive inspection and surgery inside the abdominal cavity. In standard laparoscopic surgery, a patient's abdomen is insufflated with gas, and cannula sleeves are passed through small (generally ½ inch or less) incisions to provide entry ports for laparoscopic surgical instruments. The laparoscopic surgical instruments generally include a laparoscope (a type of endoscope adapted for viewing the surgical field in the abdominal cavity) and working tools. The working tools are similar to those used in conventional (open) surgery, except that the working end or end effector of each tool is separated from its handle by a tool shaft. As used herein, the term "end effector" means the actual working part of the surgical instrument and can include clamps, graspers, scissors, staplers, image capture lenses, and needle holders, for example. The end effector for the laparoscope may include lenses and light sources that may be optically couple to a camera and lamps through the tool shaft. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in other types of surgeries such as arthroscopy, retroperitoneoscopy, pelviscopy, nephroscopy, cystoscopy, cisternoscopy, sinoscopy, hysteroscopy, urethroscopy, and the like.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION OF THE INVENTION

The detailed description describes the invention as it may be used in a laparoscopic surgery. It is to be understood that this is merely one example of the types of surgeries in which the invention may be used. The invention is not limited to laparoscopy nor to the particular structural configurations shown which are merely examples to aid in the understanding of the invention. Traditional minimally invasive surgery requires a high degree of surgical skill because the surgeon's hand movements are controlling a surgical tool at a substantial distance from the surgeon's hands, often requiring unnatural and non-intuitive hand motions. In robotically assisted surgery, a surgeon may operate a master controller to control the motion of surgical instruments at the surgical site. Servo mechanisms may move and articulate the surgical instrument based on the surgeon's manipulation of the hand input devices. The robotic assistance may allow the surgeon to control the motion of surgical instruments more easily and with greater precision.

Figure 1:
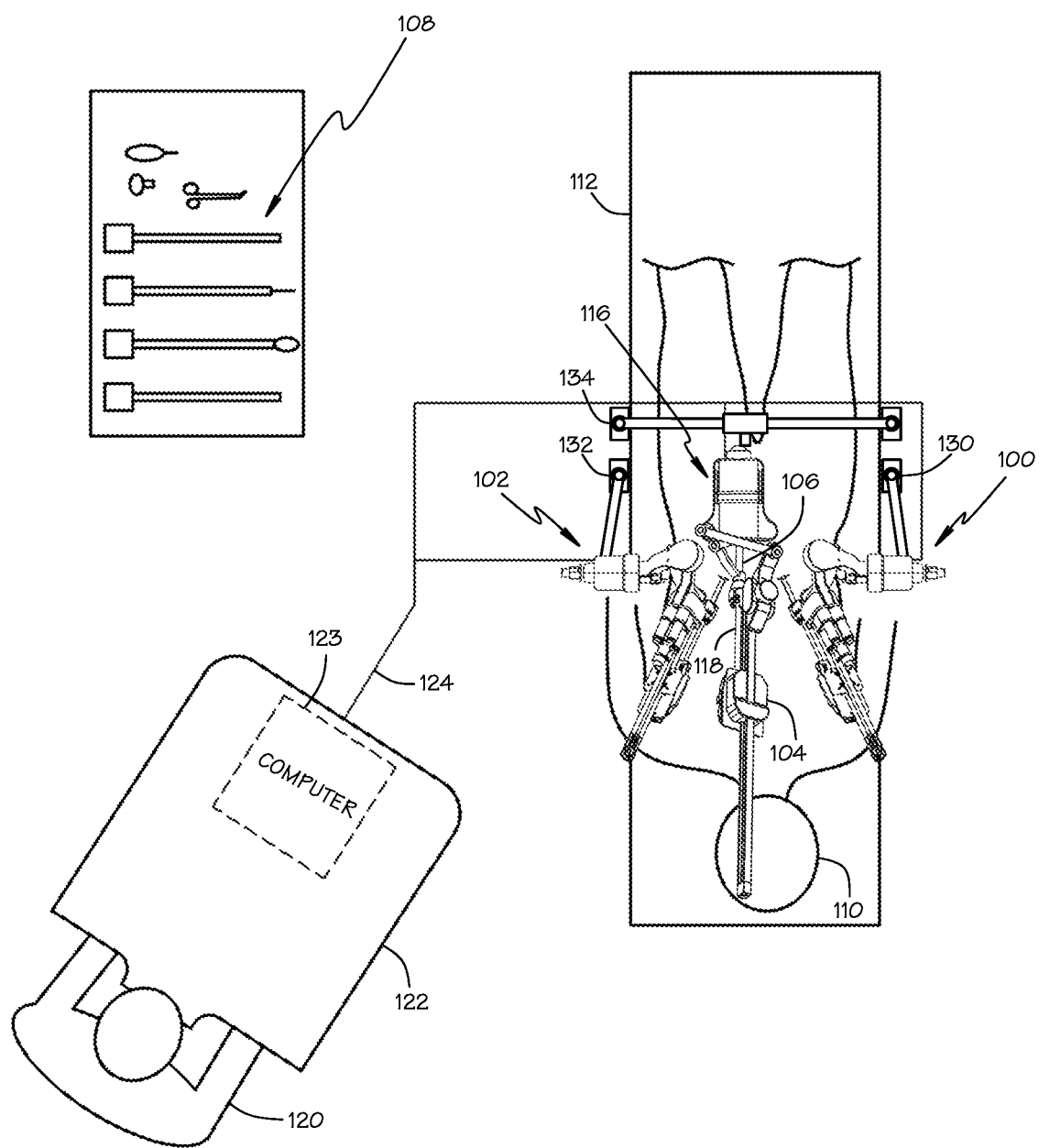
FIG. 1 is a plan view of a surgical suite in which embodiments of the invention are used.

FIG. 1 shows a schematic plan view of a surgical suite in which the invention may be used. A patient 110 is shown on an operating table 112 undergoing robotically assisted laparoscopic surgery. A surgeon 120 may use a master controller 122 to view a video image of the internal surgical site provided by an endoscopic camera, a laparoscopic camera 104 in the case of abdominal surgery, and control one or more surgical instruments and the endoscopic camera by means of robotic servo mechanisms. The master controller 122 will typically include one or more hand input devices (such as joysticks, exoskeletal gloves, or the like) which are coupled by a servo mechanism to a surgical instrument.

A robotic arm 116 that embodies the invention may be used to support and move the laparoscopic camera 104 at the surgical site during robotically assisted surgery. It is desirable to support the laparoscopic camera 104 such that the tool shaft 118 of the instrument and the cannula 106 through which it passes pivot about a center of spherical rotation positioned in space along the length of the tool shaft and cannula. Additional robotic arms 100, 102 may support and move surgical instruments. The robotic arms 100, 102 for supporting the surgical instruments may be of a different form than the robotic arm 116 for supporting the laparoscopic camera.

Each robotic arm 100, 102, 116 may be supported by an articulated set-up arm 130, 132, 134. The set-up arms may be attached to the operating table 112. Each set-up arm may include a number of segments coupled by joints that provide one or more degrees of freedom that allow the robotic arm to be positioned within a defined range of motion. One or more locking mechanisms may be provided to fix the segments and joints of the set-up arm when the robotic arm is in the desired position. The set-up arms may allow the robotic arms 100,102, 116 to be fixed at an arbitrary position with respect to the operating table and the patient thereon. Joint angle sensors may be provided on the set-up arm to allow the pose of the set-up arm and the resulting position of the supported robotic arm to be determined.

Each robotic arm 100, 102, 116 may be fixed at a position where the center of spherical rotation is substantially at the access point to the internal surgical site (for example, with the incision that provides entry for the trocar or cannula 106 at the abdominal wall during laparoscopic surgery). An end effector of the surgical instrument 104 supported by the robotic arm 116 can be positioned safely by moving the proximal end of the tool shaft 118 with the robotic arm 116 without imposing dangerous forces against the abdominal wall.

Each robotic arm 100, 102, 116 will support one surgical instrument which may be detachable from the robotic arm. While a variety of surgical instruments 108 may replace the surgical instrument on the robotic arm 100, 102 during the course of a single surgery, the laparoscopic camera 104 is generally left in place throughout the course of a surgery. Each robotic arm 116 may support a cannula 106 that passes through an incision into the body of the patient 110. The tool shaft 118 of the surgical instrument or laparoscopic camera 104 passes through the cannula 106 to the internal surgical site.

The robotic arm 116 may support the laparoscopic camera 104 such that the cannula 106 and the tool shaft 118 of the instrument pivot about a center of spherical rotation positioned in space along the length of the cannula 106. The center of spherical rotation may also be called the remote center of spherical rotation because it is the spherical center of rotational motion for the robotic arm while being spaced apart from the structure of the robotic arm. Motion about the center of spherical rotation may be described as spherical motion because a point at a radial distance from the center of spherical rotation will move on a spherical surface having the radial distance as its radius. The cannula 106 defines an insertion axis that passes through an access point, such as an incision in the abdominal wall of the patient 110, to the internal surgical site. The tool shaft 118 extends along the insertion axis.

Each robotic arm 100, 102, 116 may include one or more servo motors to move the arm to a desired position. Each robotic arm may include one or more additional servo motors to move the surgical instrument or laparoscopic camera 104 and/or an end effector on the surgical instrument or laparoscopic camera. One or more control cables 124 may provide signals between the computer 123 in the master controller 122 and the servo motors of the robotic arms 100, 102, 116. The master controller 122 may include a computer 123 to provide signals that control the servo mechanisms of the robotic arms, the surgical instruments, and laparoscopic camera based on the surgeon's input and received feedback from the servo mechanisms.

Figure 2:
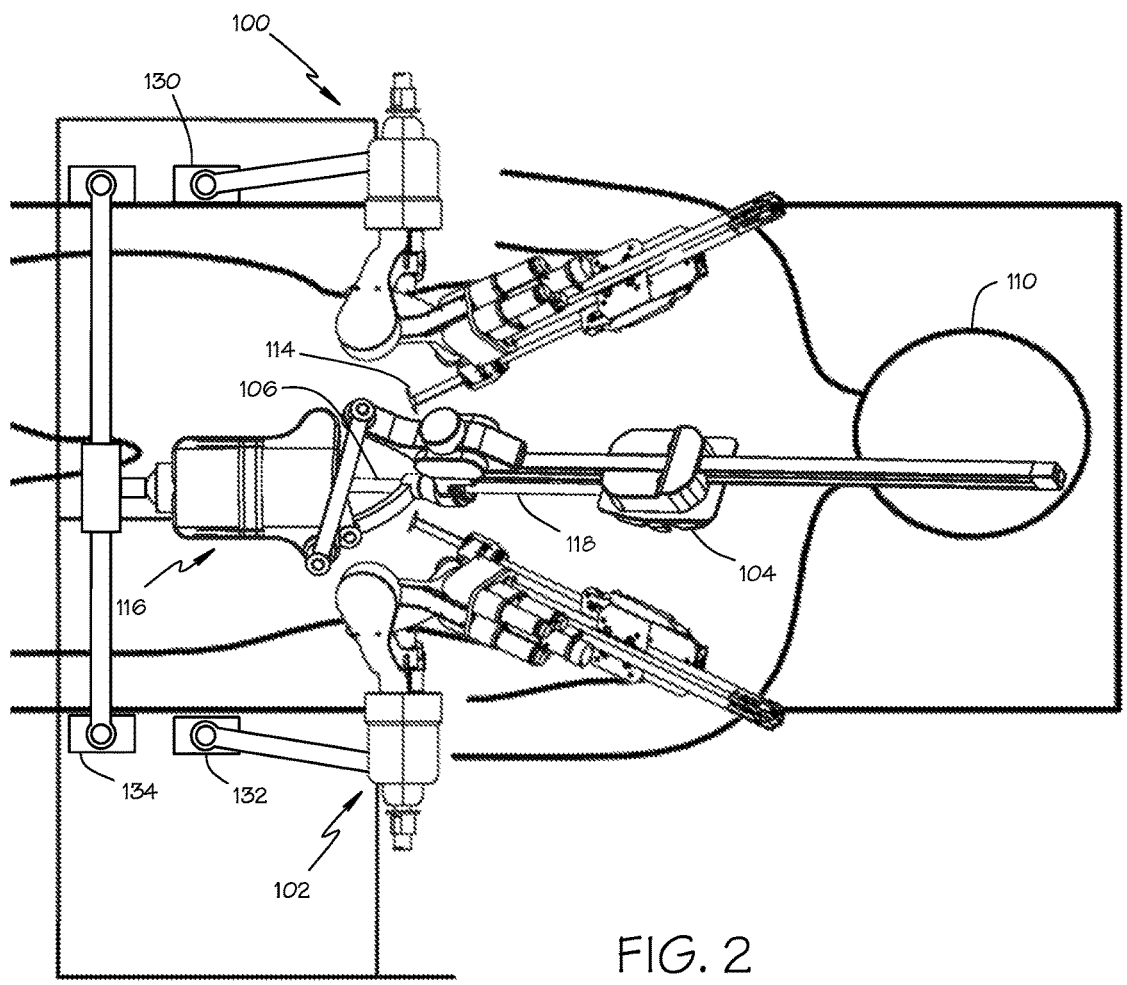
FIG. 2 is a plan view of a portion of the operating suite of FIG. 1.
Figure 3:
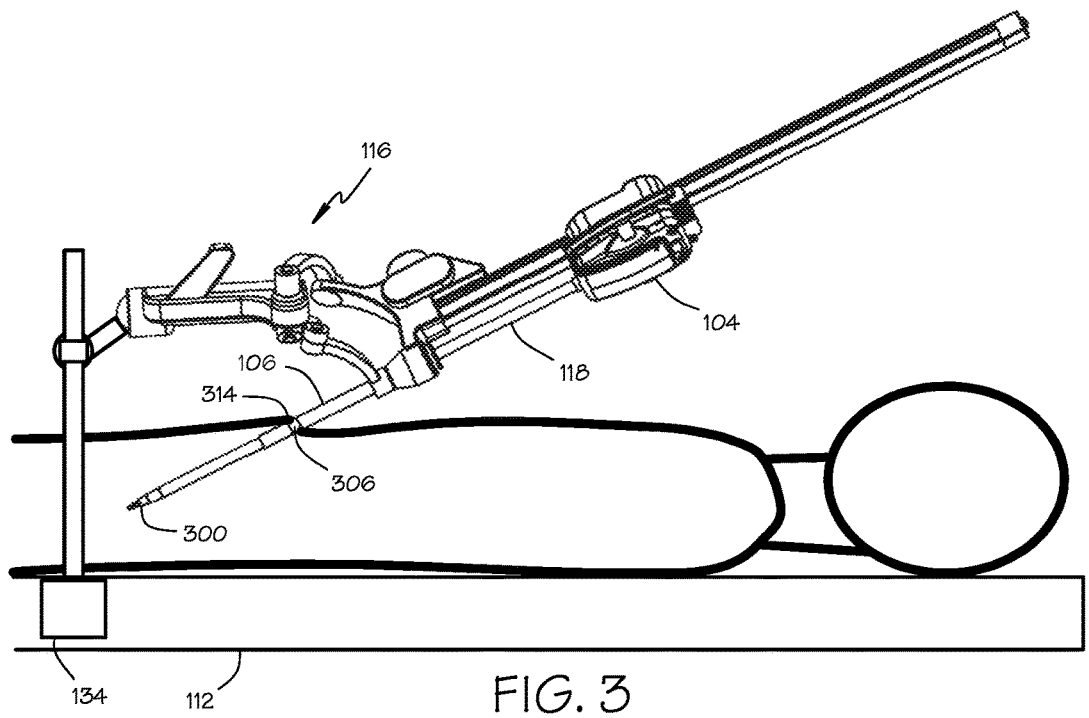
FIG. 3 is a side view of a portion of the operating suite of FIG. 2.

FIG. 2 shows an enlarged view of a portion of FIG. 1 including the patient 110 and the robotic arms 100, 102, 116. FIG. 3 shows an side view of the robotic arm 116 that supports and moves the laparoscopic camera looking from the patient's left hand side. A schematic crosssection of the patient 110 is shown in the area where the cannula 106 is inserted through an incision 314 in the abdominal wall. The tool shaft 118 of the laparoscopic camera 104 may be seen emerging from the end of the cannula 106 internal to the patient 110. An end effector 300 at the distal end of the tool shaft 118 may provide lenses and light sources. The lenses and light sources may be optically coupled to a camera and lamps through the tool shaft. The camera and lamps may be supported by the robotic arm 116 at a proximal end of the tool shaft.

The robotic arm 116 includes a spherical linkage to support the laparoscopic camera, as will be discussed in greater detail below. The spherical linkage constrains the motion of the insertion axis to rotation about a remote center of spherical rotation 306 which may be located along the length of the cannula 106. By locating the remote center of spherical rotation 306 at or near the incision 314, the insertion axis may be moved without significant lateral motion at the incision.

The end effector 300 is passed through the cannula 106 to the internal surgical site along the insertion axis. The end effector 300 is supported by the tool shaft 118 and coupled to one or more of cameras, lamps, and servo mechanisms through the tool shaft. Translation of the end effector 300 may be accomplished by translation of the laparoscopic camera 104 with the tool shaft 118 and attached end effector.

The end effector 300 may be moved in two additional dimensions by moving the tool shaft 118 about its remote center of spherical rotation 306. The robotic arm 116 will control these two dimensions of motion by moving the tool shaft 118 to change its angular position in space. The motion of the tool shaft 118 may be described in terms of the position of the insertion axis in a spherical coordinate system. A point in space may be specified in terms of two angles and a distance from a center of a spherical coordinate system. It will be appreciated that only the two angles are necessary to specify an insertion axis that passes through the center of the spherical coordinate system.

The robotic arm 116 of the present invention includes a parallel spherical five-bar linkage to move and support the laparoscopic camera 104 such that the tool shaft 118 of the instrument pivots about a remote center of spherical rotation 306 positioned in space along the insertion axis and generally along the length of the cannula 106.

Figure 4A:
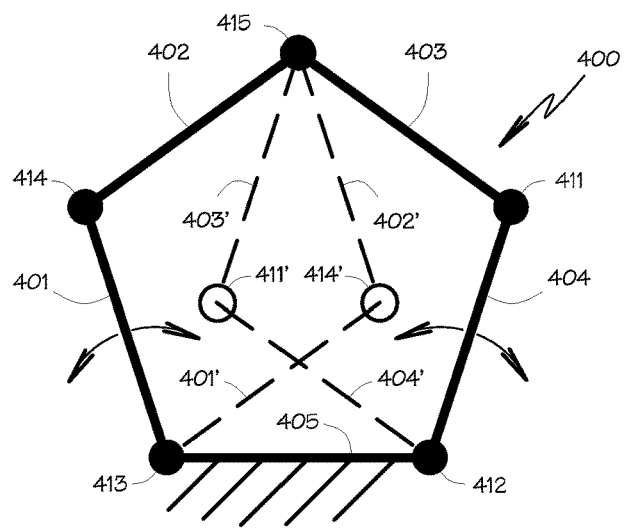
FIG. 4A is a schematic view of a parallel five-bar linkage in a first pose.

FIG. 4A shows a simplified, 2-dimensional schematic diagram of a parallel five-bar linkage 400. This example illustrates the linkage operating in essentially a flat plane. The inventive linkage operates similarly in 3-dimensional space and will be described subsequently. A parallel five-bar linkage is a system of four rigid bars or links 401, 402, 403, 404 pivoted to each other and to a fixed base link 405. The fixed base link may be referred to as the ground link. It is to be understood that the ground link 405 is fixed only in the sense that it provides a fixed frame of reference for the remaining four links. The ground link 405 may be positioned in space to move the entire five-bar linkage 400.

Each link includes two pivot axes. In the present invention, there is a substantial distance between the two pivot axes on each link. All of the pivot axes 411, 412, 413, 414, 415 are perpendicular to a common surface. The links are coupled at the pivot axes such that the links can rotate relative to each other about the pivot axis at which they are coupled. The rotatable coupling of the links at a pivot axis can take any of a variety of forms that limits the motion of the coupled links to rotation about the pivot axis. A number of axes are described for the parallel spherical five-bar linkage. The term "axis" may be used interchangeably to refer to a "joint" or a "pivot" except for the insertion axis.

The ground link 405 provides two inboard axes 412, 413. An inboard link 401, 404 is pivotally coupled to each of the inboard axes 413, 412. Each inboard link 401, 404 has an intermediate axis 414, 411 spaced apart from the inboard axis 413, 412. Each inboard link 401, 404 is pivotally coupled to an outboard link 402, 403 at the intermediate axis 414, 411. Each outboard link 402, 403 has an outboard axis 415 spaced apart from the intermediate axis 414, 411. The two outboard links 402, 403 are pivotally coupled together at the outboard axis 415. The outboard axis 415 can be positioned perpendicular to the common surface (in this 2-dimensional illustrative example) anywhere within its range of motion thus providing an endpoint motion at the outboard axis 415 with two degrees of freedom. If motors are provided to rotate each of the inboard links 401, 404 about their inboard axis 413, 412, as suggested by the arrows, the outboard axis 415 may be positioned anywhere within its range of motion by rotating the two inboard links with the motors. Conversely, movement of the outboard axis 415 within its range of motion translates into rotation of the two inboard links 401, 404 about their inboard axis 413, 412.

A linkage that couples rotation of two ground-referenced independent links with two dimensional movement of an axis is a parallel linkage. The rotary motion provided by the two motors to the two inboard links may be described as parallel rotary motion inputs. It should be noted that "parallel" is used here to indicate two inputs that are provided independently of one another and not in the geometric sense to indicate the direction of the inputs. In a parallel linkage, the two independent parallel inputs act upon the same body at some distal point where links coupled to the inputs join to drive the same object or link.

It will be appreciated that there are two possible positions for each of the inboard links 401, 404 in a five-bar linkage for most of the possible positions of the outboard axis. For example, the inboard links 401, 404 could also be positioned as indicated by the dashed lines 401', 404'. These positions for the inboard links are generally considered undesirable because the distance between the intermediate axes 414', 411' is reduced and the angle between the outboard links 402', 403' is reduced. It is normally desirable to maximize the distance between the intermediate axes to provide a broad base of support for the outboard axis 415. It is also normally desirable to have the outboard links 402', 403' as close to being at right angles to one another as possible to support the outboard axis 415. While the conventional configuration of a five-bar linkage provides good structural support for the outboard axis 415, the resulting structure requires a substantial amount of space in which to move. The alternative configuration as indicated by the links 401', 402', 403', 404' drawn with dashed lines occupies a smaller area (as projected onto the plane) and is therefore a more compact mechanical configuration.

Figure 4B:
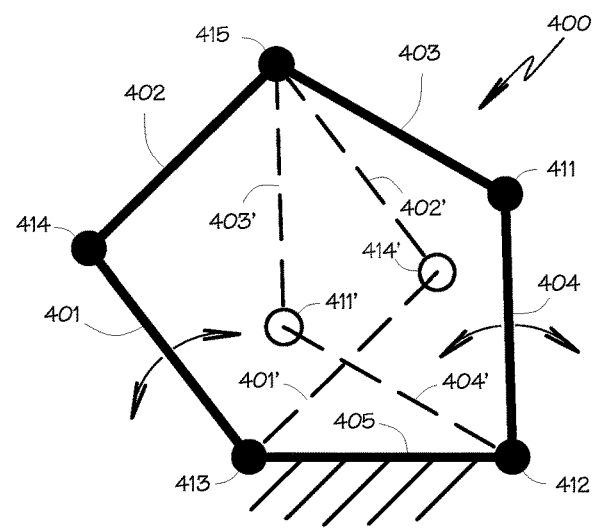
FIG. 4B is a schematic view of the parallel five-bar linkage of FIG. 4A in a second pose.

FIG. 4B shows the parallel five-bar linkage 400 after the inboard links 401, 404 have been rotated in a counterclockwise direction. It may be seen that the outboard axis 415 has been moved generally to the left by the rotation of the inboard links 401, 404. The same position of the outboard axis 415 may also be produced by a similar rotation of the inboard links 401', 404' when the parallel five-bar linkage 400 is in the compact mechanical configuration illustrated by the dashed lines.

A spherical linkage for the purposes of this description is a 3-dimensional version of the 2-dimensional mechanical linkage described above. In the 3-dimensional linkage, all pivot axes pass through a common remote center of spherical rotation. "Pass through" includes axes that may be slightly displaced (due to slight errors in manufacturing of the physical links, for example) from the remote center of spherical rotation to accommodate the structural limitations of the robotic arm where the displacement is small enough that the linkage has substantially the same kinematics (characteristic motions) as if the axes actually included the precise, theoretical remote center of spherical rotation. Note that axes that pass through a remote center of spherical rotation are also perpendicular to a spherical surface centered on the remote center of spherical rotation.

Figure 5:
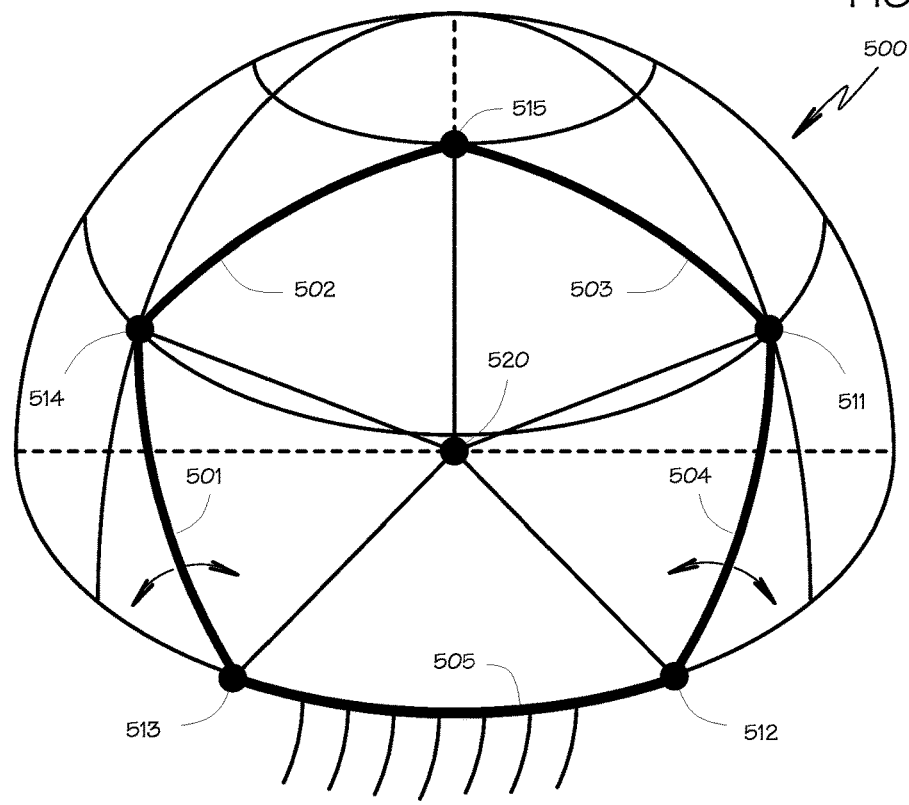
FIG. 5 is a schematic view of a parallel spherical five-bar linkage.

FIG. 5 shows a schematic diagram of a parallel spherical five-bar linkage 500. As with the previously discussed planar five-bar linkage, the parallel spherical five-bar linkage 500 is a system of four rigid links 501, 502, 503, 504 pivoted to each other and to a fixed base or ground link 505. When a parallel five-bar linkage is constructed in a spherical form, all of the pivot axes 511, 512, 513, 514, 515 are perpendicular to a common spherical surface and therefore pass through a remote center of spherical rotation 520 of the common spherical surface. In particular, the outboard axis 515 will always pass through the remote center of spherical rotation 520 within its range of motion. Thus, a parallel spherical five-bar linkage 500 provides the desired constrained motion for a surgical instrument such that the tool shaft of the instrument pivots about a remote center of spherical rotation when supported and moved by the outboard axis 515 of the linkage 500. The motors to move the surgical instrument are placed at the inboard axes 513, 512 of the ground link 505. This avoids the need to move one motor with the other motor as might be required if a serial arm mechanism were used.

Figure 6A:
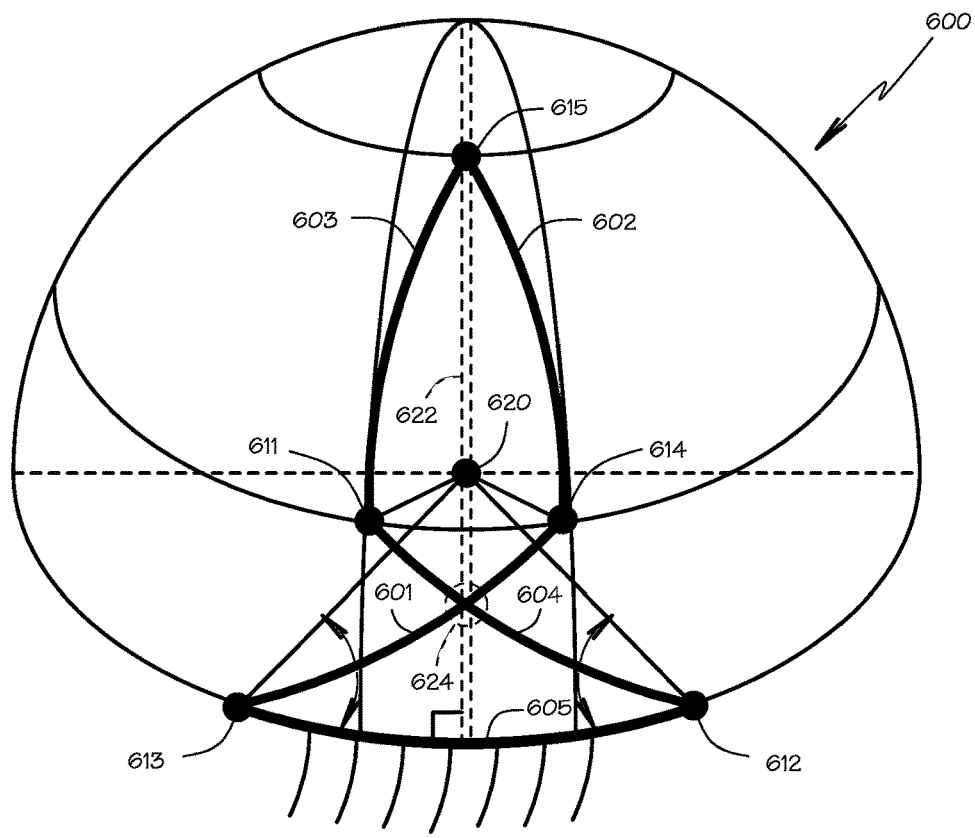
FIG. 6A is a schematic view of another parallel spherical five-bar linkage in a first pose.

As shown schematically in FIG. 6A, it has been discovered that a parallel spherical five-bar linkage 600 can be constrained so that the intermediate axes 614, 611 do not assume the conventional configuration where the intermediate axes are at their maximum possible separation and, surprisingly, provide good structural support for the outboard axis 615. This results in a more compact configuration that is better suited for use as a robotic arm to support an endoscopic camera where it is often necessary to have other robotic arms in close proximity within a limited amount of space as shown by the exemplary system in FIGS. 1 and 2.

The parallel spherical five-bar linkage 600 shown schematically includes a ground link 605, two inboard links 601, 604 pivotally coupled to the ground link, and two outboard links 602, 603 pivotally coupled to each other at one end and to the two inboard links 601, 604 respectively at an opposite end. The first inboard link 601 is pivotally coupled to the ground link 605 at a first axis of rotation 613. The first inboard link 601 further includes a first intermediate axis 614 at a first distance from the first axis of rotation 613. A first outboard link 602 is pivotally coupled to the first inboard link 601 at the first intermediate axis 614. The first outboard link 602 has an outboard axis 615 at a second distance from the first intermediate axis 614.

The second inboard link 604 is pivotally coupled to the ground link at a second axis of rotation 612. The second inboard link 604 has a second axis of rotation 612 that is separated from the first axis of rotation 613 by a fourth distance. The second inboard link 604 further includes a second intermediate axis 611 at a fifth distance from the second axis of rotation 612. A second outboard link 603 is pivotally coupled to the second inboard link 604 at the second intermediate axis 611 and to the first outboard link 602 at the outboard axis 615. The outboard axis 615 is at a sixth distance from the second intermediate axis 611.

A mechanical stop may limit the rotation of the outboard links 602, 603 about the outboard axis 615 such that a minimum angle is maintained between the outboard links, perhaps a minimum angle in the range of 15 to 30 degrees. The links are assembled and constrained such that when the outboard axis 615 lies in a plane 622 that is the perpendicular bisector of the line segment from the first axis of rotation 613 to the second axis of rotation 612, each of the inboard links 601, 604 intersects 624 the bisecting plane 622. (The double dashed lines are intended to suggest an edge of the portion of the imaginary bisecting plane 622 in the vicinity of the linkage 600. The dashed circle indicates the point of intersection between each of the inboard links 601, 604 and the bisecting plane 622, which is at the same place for the configuration and pose shown.) When an inboard link intersects the bisecting plane, the axis of rotation and the intermediate axis will lie on opposite sides of the plane. It will be appreciated that this requires the inboard links 601, 604 to be able to cross over one another.

A specific position assumed by a robotic arm may be referred to as a pose. Placing a robotic arm in a specific position may be referred to as posing the robotic arm. The parallel spherical five-bar linkage may be limited in its motion such that the two intermediate axes 614, 611 are relatively close together compared to the maximum separation possible for any given pose of the robotic arm 600. In particular, each inboard link 601, 604 may be in one of two positions for a given position of the outboard axis 615, except for the singularities where the axis of rotation 612, 613, the intermediate axis 611, 614, and the outboard axis 615 are coplanar. One of the two positions for each of the two inboard links 601, 604 will provide the maximum distance between the intermediate axes 611, 614. The pose where each of the two inboard links 601, 604 is in the other of the two positions will be described as the compact pose. It will be appreciated that this always results in less than the maximum distance between the intermediate axes 611, 614 although it may not result in the minimum possible distance. If the outboard links are constrained to maintain at least a minimum angle between the outboard links and the parallel five-bar spherical linkage is assembled in a compact pose, then the linkage will be limited to a range of compact poses.

Figure 6B:
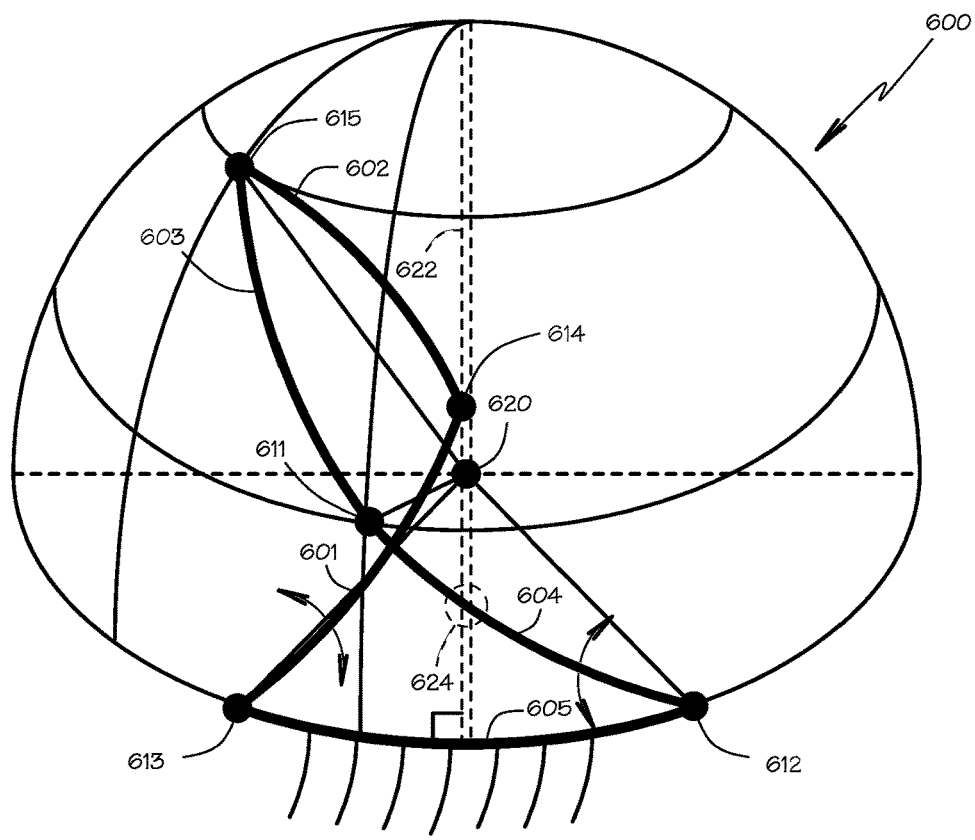
FIG. 6B is a schematic view of the parallel five-bar linkage of FIG. 6A in a second pose.

FIG. 6B shows the parallel spherical five-bar linkage 600 after one of the inboard links 601 has been rotated in a counter-clockwise direction. It may be seen that the outboard axis 615 has been moved generally to the left by the rotation of the inboard link 601. It may also been seen that points on the outboard axis 615 are constrained to move on a spherical surface. In the pose shown in FIG. 6B neither of the two inboard links 601, 604 intersect the bisecting plane 622. It will be observed that the linkage 600 retains the compact configuration even though it has moved away from the pose where the outboard axis 615 lies in a plane 622 that is the perpendicular bisector of the line segment from the first axis of rotation 613 to the second axis of rotation 612.

Figure 7A:
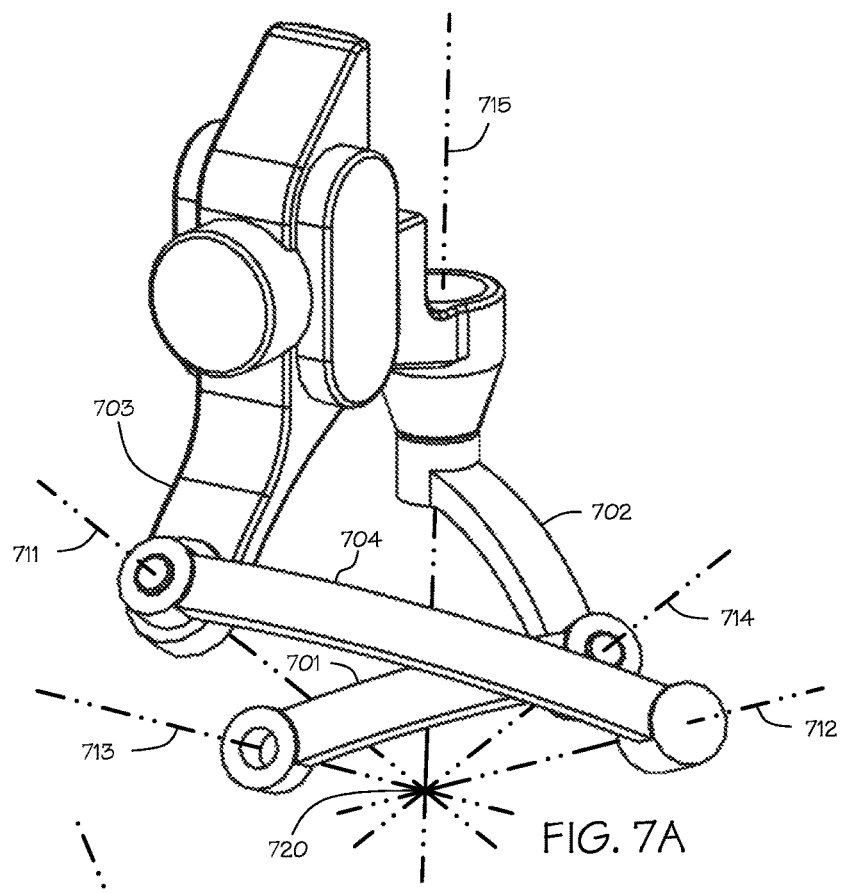
FIG. 7A is a pictorial view of an embodiment of the invention in a first pose.

Referring now to FIG. 7A, the inboard links 701, 704 and the outboard links 702, 703 are illustrated for the embodiment shown in FIGS. 1-3. The ground link, which is provided by a motor assembly, is not shown in FIG. 7 to allow the relationship between the four moving links to be better seen. The two inboard links 701, 704 each can rotate about one of the axes of rotation 713, 712. Each inboard link 701, 704 is pivotally coupled to an outboard link 702, 703 at an intermediate axis 711, 714. The two outboard links 702, 703 are pivotally coupled together at an outboard axis 715. The outboard axis 715 may also be the insertion axis on which the cannula (not shown) is centered.

In some embodiments, the first axis 713 and second axis 712 of rotation are driven by motors connected to a controller that provides signals to the motors. A first motor may rotate the first inboard link 701 and a second motor may rotate the second inboard link 704. The controller may limit the motion of the links so that the parallel five-bar spherical linkage is limited to a range of compact poses. The controller may limit the motion of the inboard links 701, 704 such that each of the inboard links 701, 704 intersects a perpendicular bisecting plane of the line segment from the first axis of rotation 713 to the second axis of rotation 712 when the outboard axis 715 lies in the bisecting plane. When an inboard link intersects the bisecting plane, the axis of rotation and the intermediate axis will lie on opposite sides of the bisecting plane. The controller may also limit the rotation of the inboard links 701, 704 such that a minimum angular distance is maintained between the intermediate axes 711, 714, perhaps a minimum angular distance in the range of 15 to 30 degrees. The controller can provide the same constraint on the range of motion of the links 701-704 as a mechanical stop that limits the angle between the outboard links 702, 703 at the outboard axis 715.

Figure 7B:
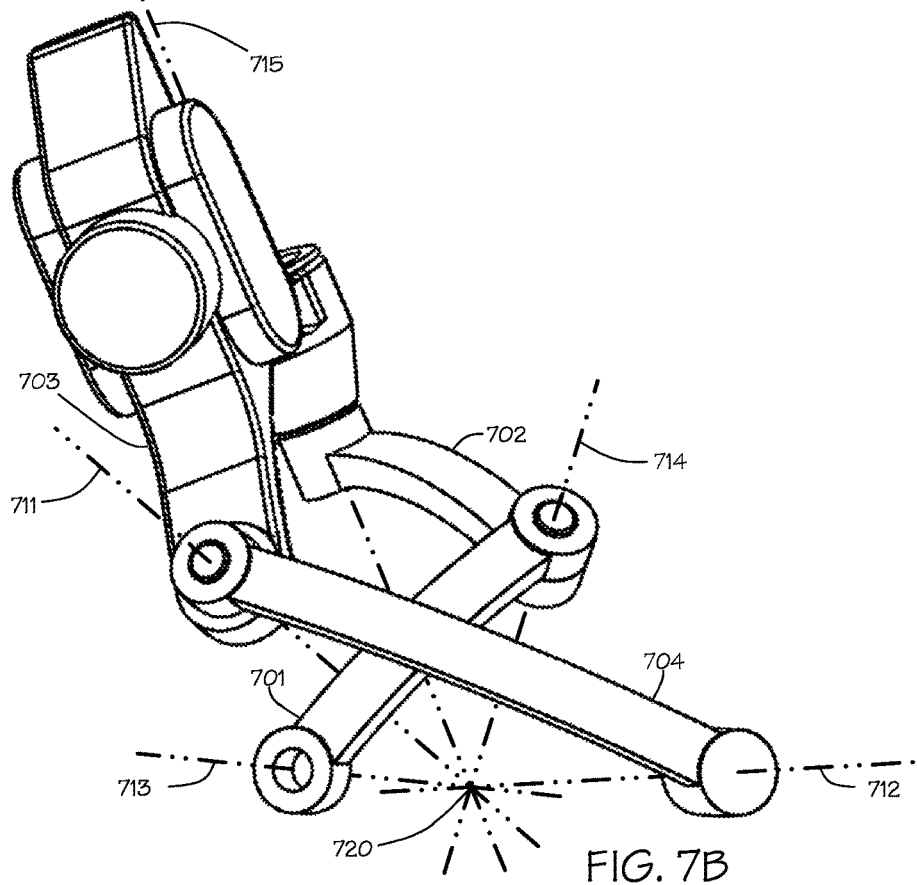
FIG. 7B is a pictorial view of the embodiment of FIG. 7A in a second pose.

The parallel spherical five bar linkage may be used to move the outboard axis 715 to a desired position by controllably rotating the inboard links 701, 704, such as by use of a servo motor or stepper motor. FIG. 7B illustrates the parallel spherical five bar linkage after one of the inboard links 701 has been rotated in a counter-clockwise direction. The poses of the parallel spherical five bar linkage shown in FIGS. 7A and 7B are generally similar to the poses of the parallel spherical five bar linkage shown schematically in FIGS. 6A and 6B respectively.

In another embodiment, the parallel spherical five bar linkage may be used to sense a position of the outboard axis by determining the bearings of the two inboard axes that result from manipulation of the outboard axis. For example, rotary encoders, or other sensors, may be placed at the first 713 and second 712 axis of rotation of the parallel spherical five bar linkage illustrated by FIG. 7. The controller may be replaced by a computer coupled to the two rotary encoders to receive the bearing of each of the inboard links 701, 704. The computer may then compute the position of the outboard axis, which may be manipulated by an operator to provide a position input. It will be appreciated that the outboard axis is constrained to rotate about the remote center of spherical rotation 720 of the spherical linkage. Thus, the parallel spherical five bar linkage may also be used in the control console 122 of FIG. 1 to receive position input for the outboard axis 715 from the surgeon 120. The position input will have the same constrained motion as the outboard axis of the robotic arm 116.

Figure 8:
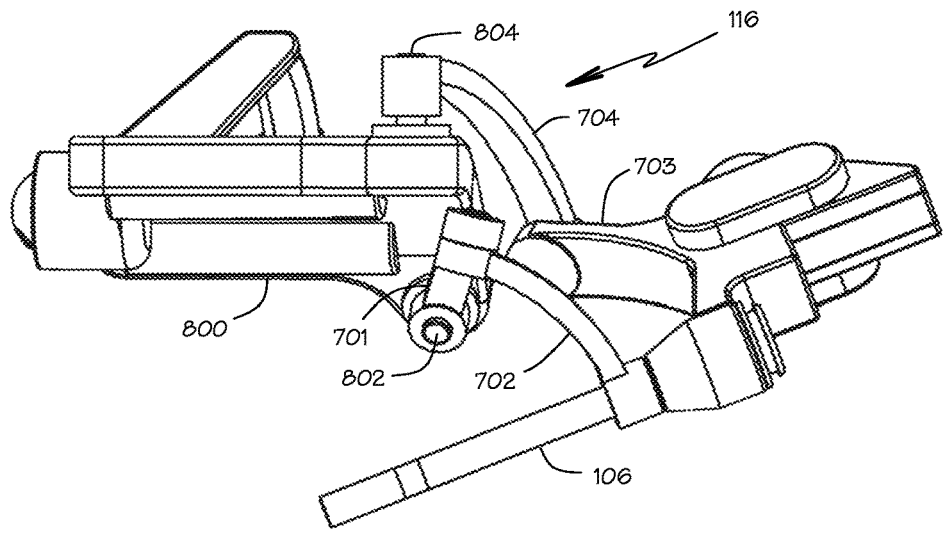
FIG. 8 is a view of a first side of an embodiment of the invention.
Figure 9:
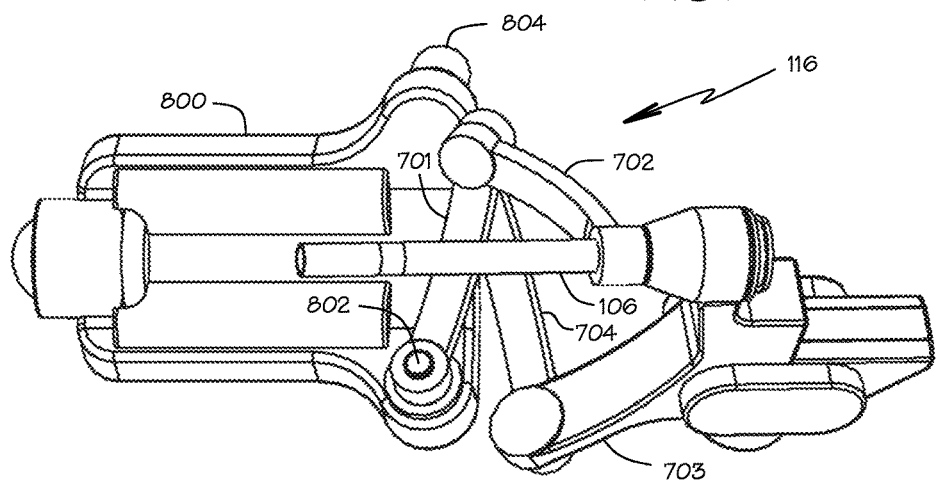
FIG. 9 is a bottom view of the embodiment of the invention shown in FIG. 8.
Figure 10:
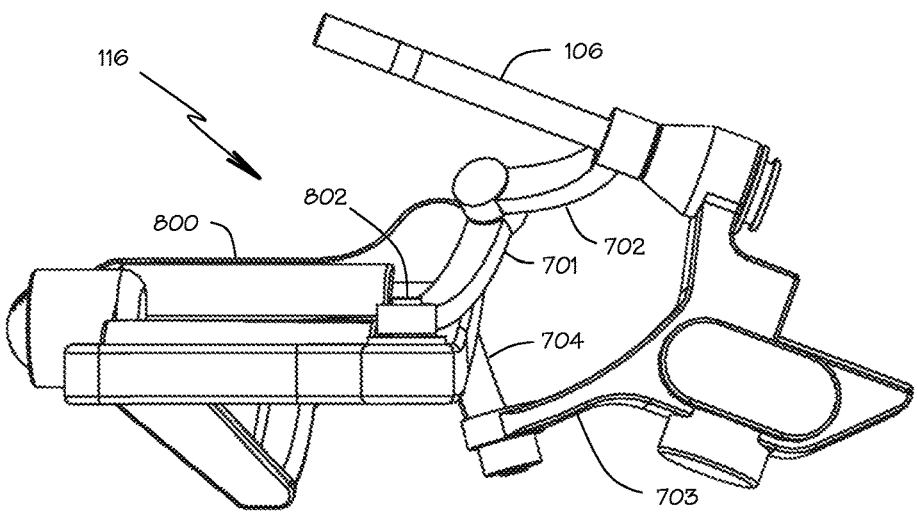
FIG. 10 is view of a second side of the embodiment of the invention shown in FIG. 8.
Figure 11:
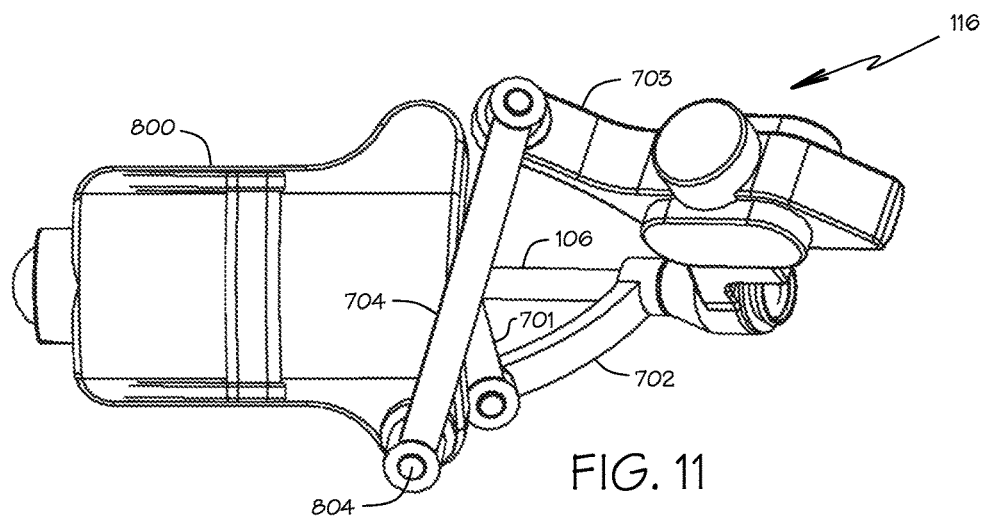
FIG. 11 is a top view of the embodiment of the invention shown in FIG. 8.
Figure 12:
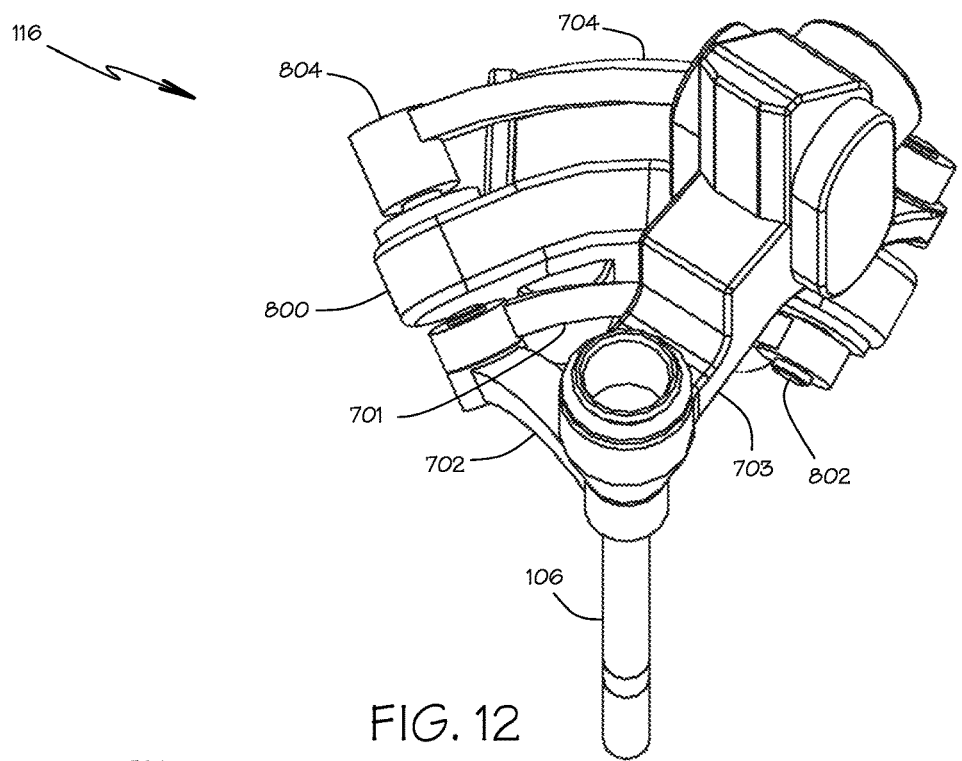
FIG. 12 is an end view of the embodiment of the invention shown in FIG. 8.

Referring now to FIGS. 8, 9, 10, 11, and 12, orthogonal views are shown for four sides and an end of the robotic arm 116 used to support the laparoscopic camera in the same pose as shown in FIGS. 1-3. FIG. 8 is a first side view. FIG. 9 is a bottom view. FIG. 10 is a second side view of the side opposite the first side. FIG. 11 is a top view. FIG. 12 is a view of the end that is to the right in FIGS. 8-11.

FIGS. 8-12 show a robotic arm 116 that embodies the invention. The robotic arm includes a motor assembly 800 that serves as a ground link and four movable links 701, 702, 703, 704 to provide a parallel spherical five bar linkage. The relationship of the four movable links was discussed above in connection with FIG. 7. The motor assembly 800 provides two rotatable shafts 802, 804. Each of the rotatable shafts is coupled to one of the two inboard links 701, 704 at one of the axes of rotation 713, 712 (shown in FIG. 7). A cannula 106 is supported by the two outboard links 702, 703 in a position that is coaxial with the outboard axis 715 (shown in FIG. 7). In this embodiment, the outboard axis 715 is coincident with the insertion axis for the tool shaft of an endoscopic camera.

Figure 13:
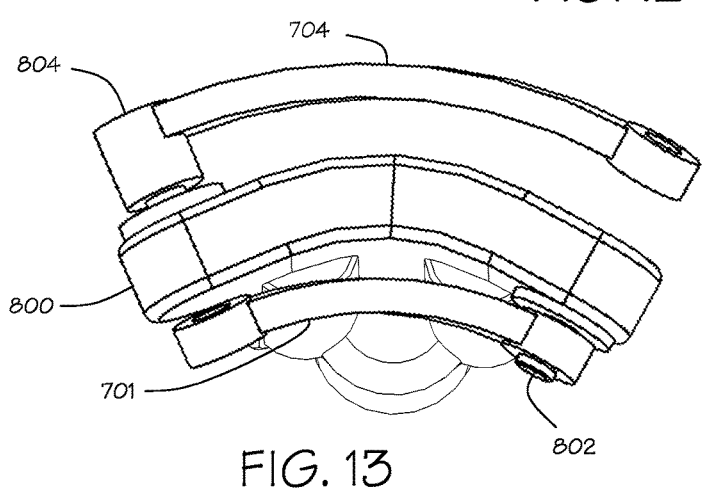
FIG. 13 is a pictorial view of a portion of the embodiment as shown in FIG. 12.

FIG. 13 shows the robotic arm 116 of FIG. 12 with the two outboard links 702, 703 removed so that the relationship between the motor assembly 800 and the two inboard links 701, 704 can be seen. The motor assembly 800 and the two inboard links 701, 704 are shaped and coupled in a configuration that allows the two inboard links to pass over one another and the motor assembly. It may be seen that the two rotatable shafts 802, 804 emerge from the motor assembly 800 in substantially opposite directions in this embodiment. The two rotatable shafts 802, 804 may be driven by motors coupled to the shafts through right angle drives, such as a worm and helix drive.

One inboard link 701 moves within a spherical "shell" that is closer to the center of spherical motion than the motor assembly. The other inboard link 704 moves within a spherical "shell" that is further from the center of spherical motion than the motor assembly. The motor assembly 800 lies between these two spherical "shells." Thus one pair of links passes the motor assembly to the inside and the other pair of links passes to the outside.

Figure 14:
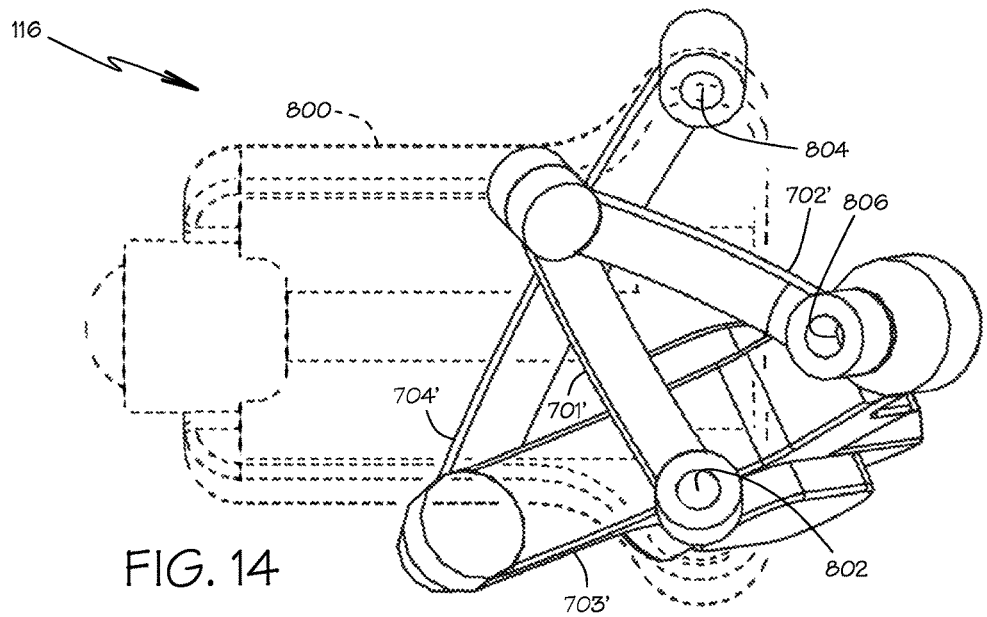
FIG. 14 is a bottom view of the embodiment of the invention as shown in FIG. 9 in a different operative position.

FIG. 14 shows the robotic arm 116' of FIG. 9 in a pose with the outboard axis 806 close to the motor assembly 800. (The motor assembly 800 is drawn as though transparent as suggested by the dashed lines to allow the configuration of the movable links 701', 702', 703', 704' to be seen.) One inboard link 701', which is coupled to a first rotatable shaft 802 that extends toward the remote spherical center, and the coupled outboard link 702' have passed to the inside of the motor assembly 800. These links lie between the motor assembly 800 and the remote spherical center. The other inboard link 704', which is coupled to a second rotatable shaft 804 that extends away from the remote spherical center, and the coupled outboard link 703' have passed to the outside of the motor assembly 800. The motor assembly 800 lies between these links and the remote spherical center.

Figure 15:
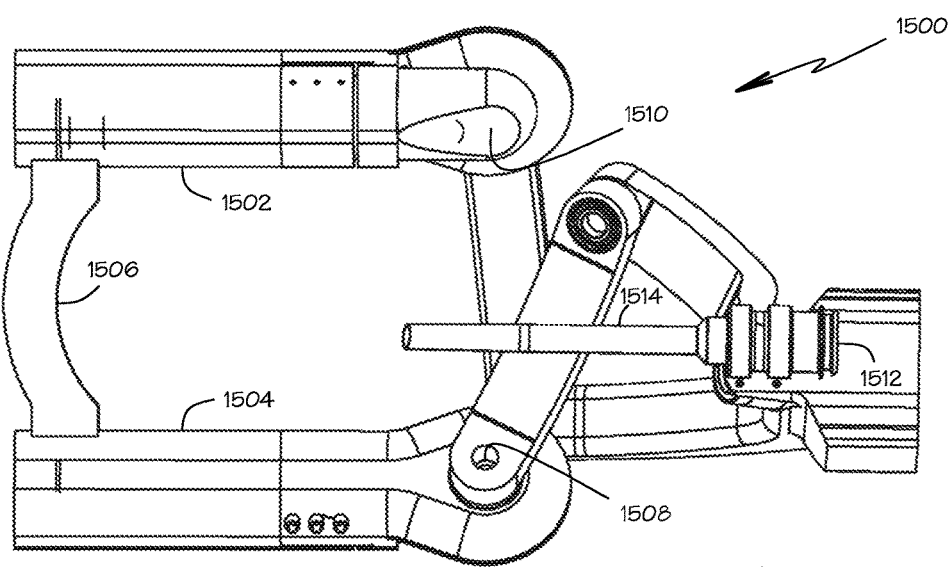
FIG. 15 is a bottom view of another embodiment of the invention.

FIG. 15 shows another robotic arm 1500 that embodies the invention. The motor assembly includes two motors 1502, 1504 that are coupled by a support 1506 at a substantial distance from the two axes of rotation 1508, 1510. The motor assembly provides the ground link for the parallel spherical five bar linkage. This configuration of the support 1506 may permit the outboard axis 1512, which may also be the axis for the cannula 1514, to pass between the two axes of rotation 1508, 1510 and the two motors 1502, 1504 to provide a greater range of motion.

Figure 16:
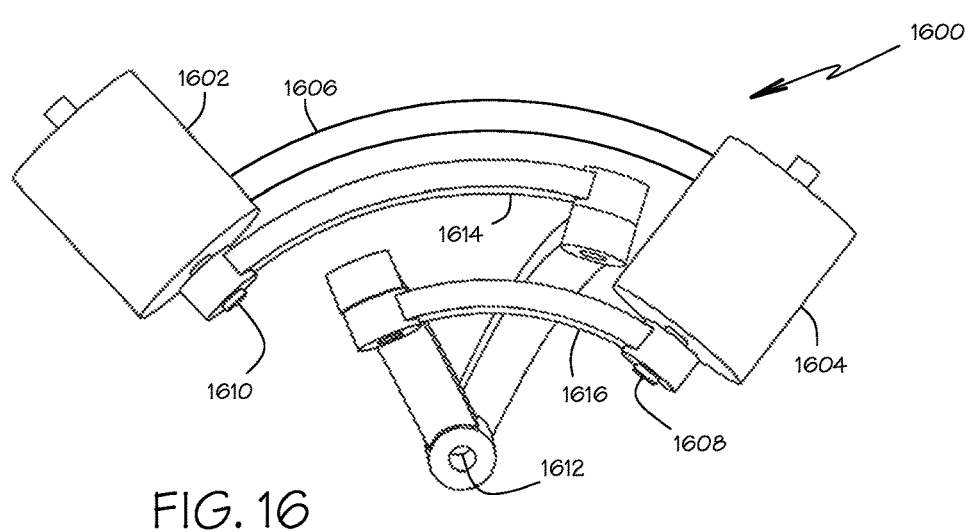
FIG. 16 is an end view of another embodiment of the invention.

FIG. 16 shows still another robotic arm 1600 that embodies the invention. The motor assembly includes two motors 1602, 1604 that are coupled by a support 1606 to provide the ground link for the parallel spherical five bar linkage. The two axes of rotation 1608, 1610 may coincide with axes of the two motors 1602, 1604 such that a right angle drive is not required. At least one of the inboard links 1614 has an angular length that is substantially less than the angular distance between the two axes of rotation 1608, 1610. This permits the inboard link 1614 to the motor 1604 that is coupled to the other inboard link 1616. The other inboard link 1616 may or may not have an angular length that is substantially less than the angular distance between the two axes of rotation 1608, 1610 as it may be configured to pass to the inside of the motor 1602, between the motor and the remote spherical center, that is coupled to the shortened inboard link 1614.

Figure 17:
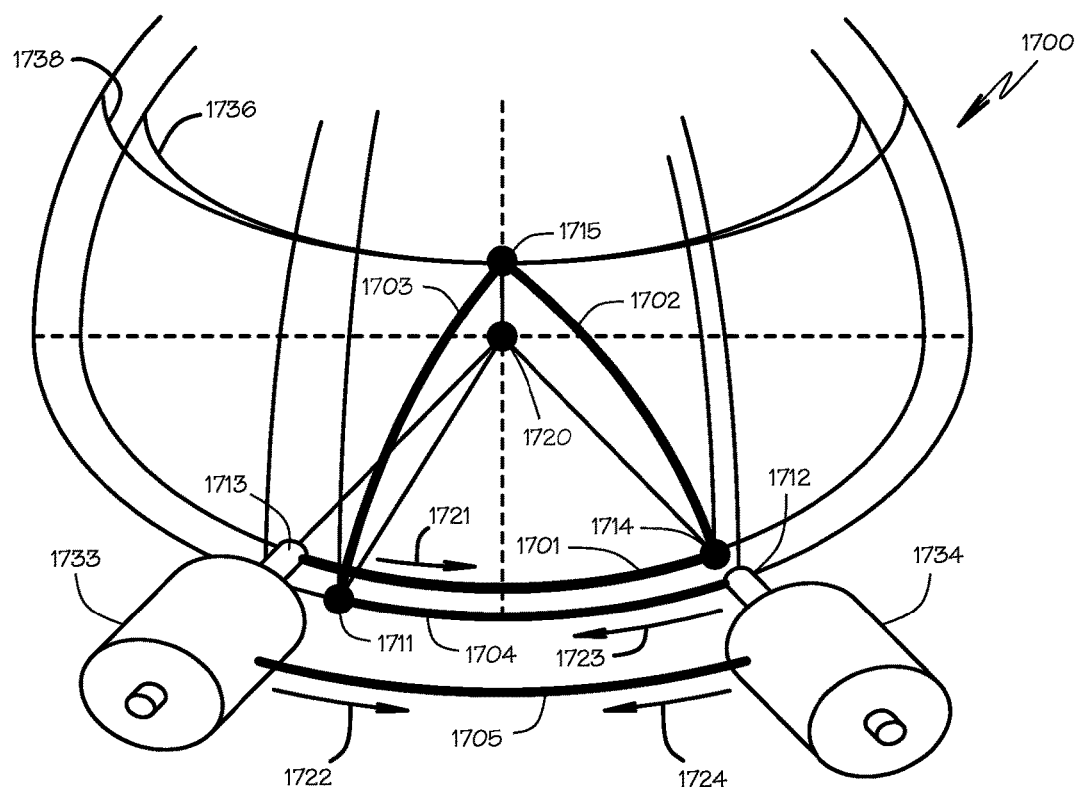
FIG. 17 is a schematic view of a parallel spherical five-bar linkage.

FIG. 17 shows a schematic representation of a robotic arm 1700 that is similar to the robotic arm 1600 shown in FIG. 16. A first pair of inboard and outboard links 1701, 1702 are pivotally coupled at a first intermediate axis 1714. A second pair of inboard and outboard links 1704, 1703 are pivotally coupled at a second intermediate axis 1711. The two outboard links 1702, 1703 are pivotally coupled at an outboard axis 1715. One of two motors 1733, 1734 is coupled to each of the inboard links 1701, 1704 to rotate the inboard link about an axis of rotation 1713, 1712. The two motors are coupled by a ground link 1705 to complete the parallel spherical five-bar linkage.

It may be observed that the first pair of inboard and outboard links 1701, 1702 may be constructed so that they move within a first spherical shell 1736. The second pair of inboard and outboard links 1704, 1703 move within a second spherical shell 1738 that is not shared with the first spherical shell 1736 except in the vicinity of the outboard axis 1715. This arrangement permits the inboard links 1701, 1704 to cross over one another. The inboard links 1701, 1704 in this arrangement may also pass to the inside, closer to the remote center of spherical rotation 1720, of the ground link 1705 that couples the two motors 1733, 1734 if the ground link lies outside the second spherical shell 1738.

The arrangement of the linkage 1700 has the further characteristic that when the first inboard link 1701 lies in the same plane as the ground link 1705 as shown, a first directional vector 1721 from the first axis of rotation 1713 to the first intermediate axis 1714 has the same direction as a second directional vector 1722 from the first axis of rotation 1713 to the second axis of rotation 1712. Likewise, when the second inboard link 1704 lies in the same plane as the ground link 1705, a third directional vector 1723 from the second axis of rotation 1712 to the second intermediate axis 1711 has the same direction as a fourth directional vector 1724 from the second axis of rotation 1712 to the first axis of rotation 1713.

Figure 18:
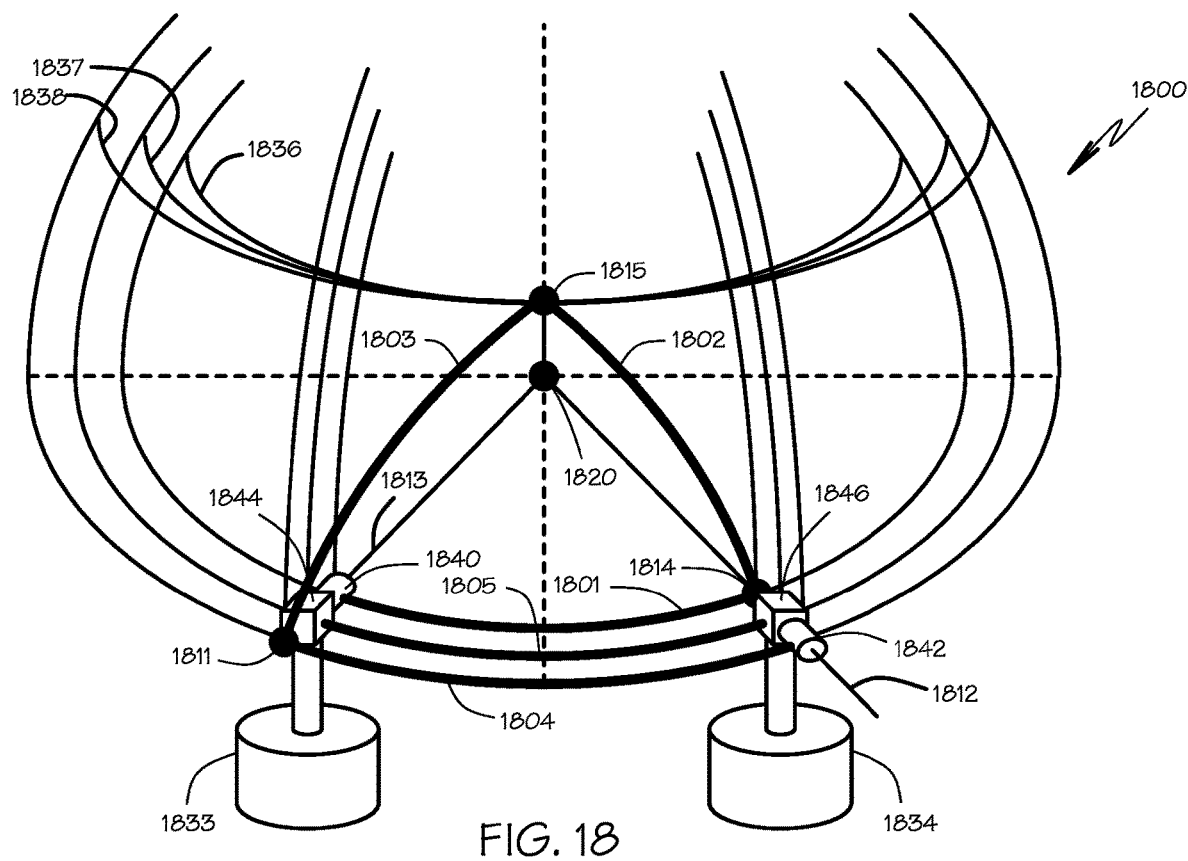
FIG. 18 is a schematic view of another parallel spherical five-bar linkage.

FIG. 18 shows a schematic representation of a robotic arm 1800 that is similar to the robotic arm 116 as shown in FIG. 11. A first pair of inboard and outboard links 1801, 1802 are pivotally coupled at a first intermediate axis 1814. A second pair of inboard and outboard links 1804, 1803 are pivotally coupled at a second intermediate axis 1811. The two outboard links 1802, 1803 are pivotally coupled at an outboard axis 1815. One of two motors 1833, 1834 is coupled to each of the inboard links 1801, 1804 to rotate the inboard link about an axis of rotation 1813, 1812. The two motors are coupled by a ground link 1805 to complete the parallel spherical five-bar linkage.

In the arrangement shown in FIG. 18, the ground link 1805 is between the two inboard links 1801, 1804 when all three links are in the same plane. The first pair of inboard and outboard links 1801, 1802 may move within a first spherical shell 1836. The second pair of inboard and outboard links 1804, 1803 may move within a second spherical shell 1838 that is not shared with the first spherical shell 1836 except in the vicinity of the outboard axis 1815. If the ground link is within a third spherical shell 1837 that lies between the first and second spherical shells, then the inboard links 1801, 1804 may cross over one another and also cross over the ground link. The arrangement of the linkage 1800 has the same directionality characteristic when the inboard links 1801, 1804 lie in the same plane as the ground link 1805 as discussed above for the linkage 1700 shown in FIG. 17.

In the arrangement shown in FIG. 18, the axes of the motors 1833, 1834 may be perpendicular to the axes of rotation 1813, 1812. This may be done to allow all or part of the motors to be within the third spherical shell 1837 over which the inboard links 1801, 1804 may pass. A drive shaft 1840, 1842 may couple the motors 1833, 1834 to inboard links 1801, 1804 by means of a right angle drive 1844, 1846. In other embodiments, the drive shaft may be coupled to the motors in other arrangements or be a coaxial extension of the motor shaft. The end of the drive shaft 1840, 1842 coupled to the motors 1833, 1834 may be described as the driven end. In the arrangement shown, it may be observed that a first drive shaft 1840 extends from the driven end toward the remote center of spherical rotation 1820 and a second drive shaft 1842 extends from the driven end away from the remote center of spherical rotation 1820.

Figure 19:
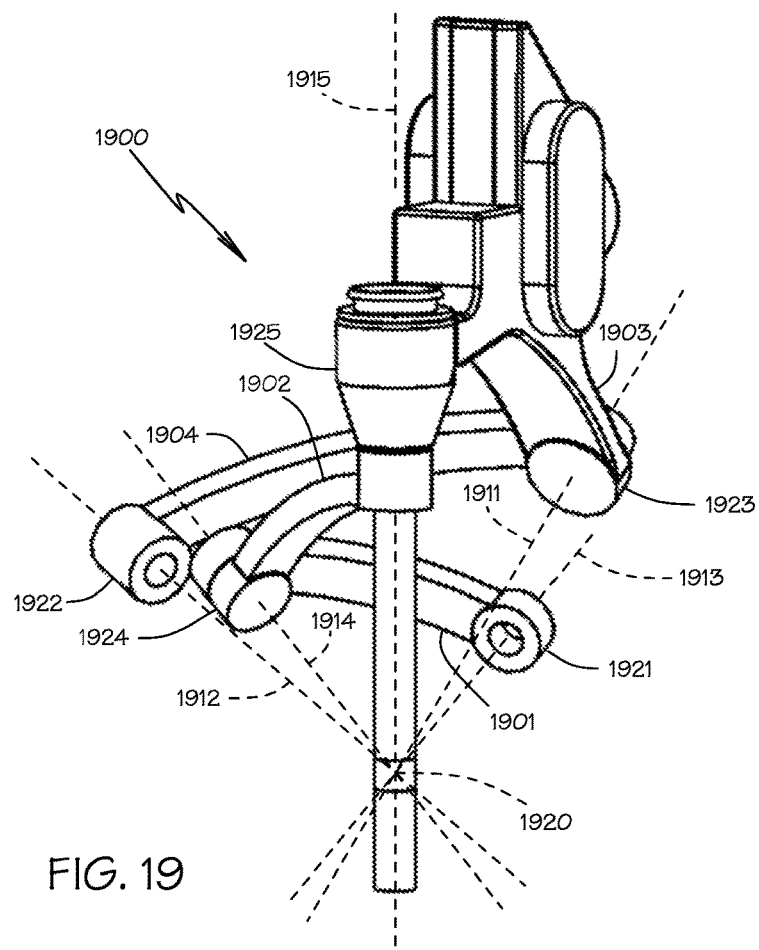
FIG. 19 is a pictorial view of another embodiment of the invention.
Figure 20:
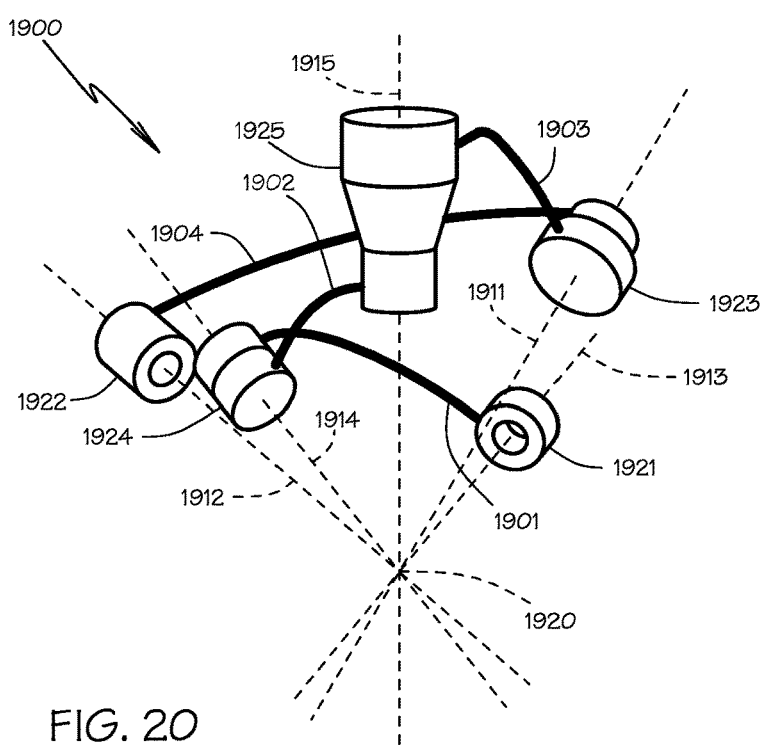
FIG. 20 is a schematic view of the parallel spherical five-bar linkage shown in FIG. 19.

FIG. 19 shows a parallel spherical five-bar linkage 1900 that embodies the invention with a structure similar to the robotic arm 116 shown in FIGS. 7-12. FIG. 20 shows a schematic view of the parallel spherical five-bar linkage 1900 of FIG. 19. Five pivot axes 1911-1915, about which the four movable links 1901-1904 rotate, all pass through a common remote center of spherical rotation 1920. The first inboard link 1901 and the second inboard link 1904 may be coupled to motors that can rotate the inboard links about the first 1913 and second 1912 axes of rotation. The two motors may be coupled together to form the fifth link (not shown), which is the ground link.

The movable links 1901, 1902, 1903, 1904 are shown as having a generally arcuate form. It will be appreciated that the links may have any desired form without affecting the function of the invention. The linkage will function as a spherical linkage as long as the axes of the pivoted connections 1921, 1922, 1923, 1924, 1925 all pass substantially through a common remote center of spherical rotation 1920. Any of the links may have an irregular shape, which may include arcuate segments, to accommodate placement of the pivoted connections such that the links and pivots can pass one another. It will be appreciated that the form of the links is unimportant as long as they support the pivot axes such that they pass substantially through the remote center of spherical rotation 1920.

In the compact configuration of the inventive parallel spherical five bar linkage, it may be desirable to configure the linkage such that the first pair of links 1901, 1902 coupling the first axis of rotation 1913 to the outboard axis 1915 can freely pass the second pair of links 1904, 1903 coupling the second axis of rotation 1912 to the outboard axis 1915. Since the only requirement of the parallel spherical five-bar linkage is that all the pivot axes pass substantially through the common remote center of spherical rotation 1920, the first pair of links 1901, 1902 and the first intermediate pivot 1914 may be configured so that a first volume swept out by the first pair does not intersect a second volume swept out by the second pair of links 1904, 1903 and the second intermediate pivot 1911. The only connections between the first and second volumes are in the vicinity of the outboard axis 1915 and the ground link 1905. The form of the links in the embodiment illustrated by FIGS. 19 and 20 are an example of a configuration that permits the first pair of links 1901, 1902 to pass the second pair of links 1904, 1903.

Figure 21:
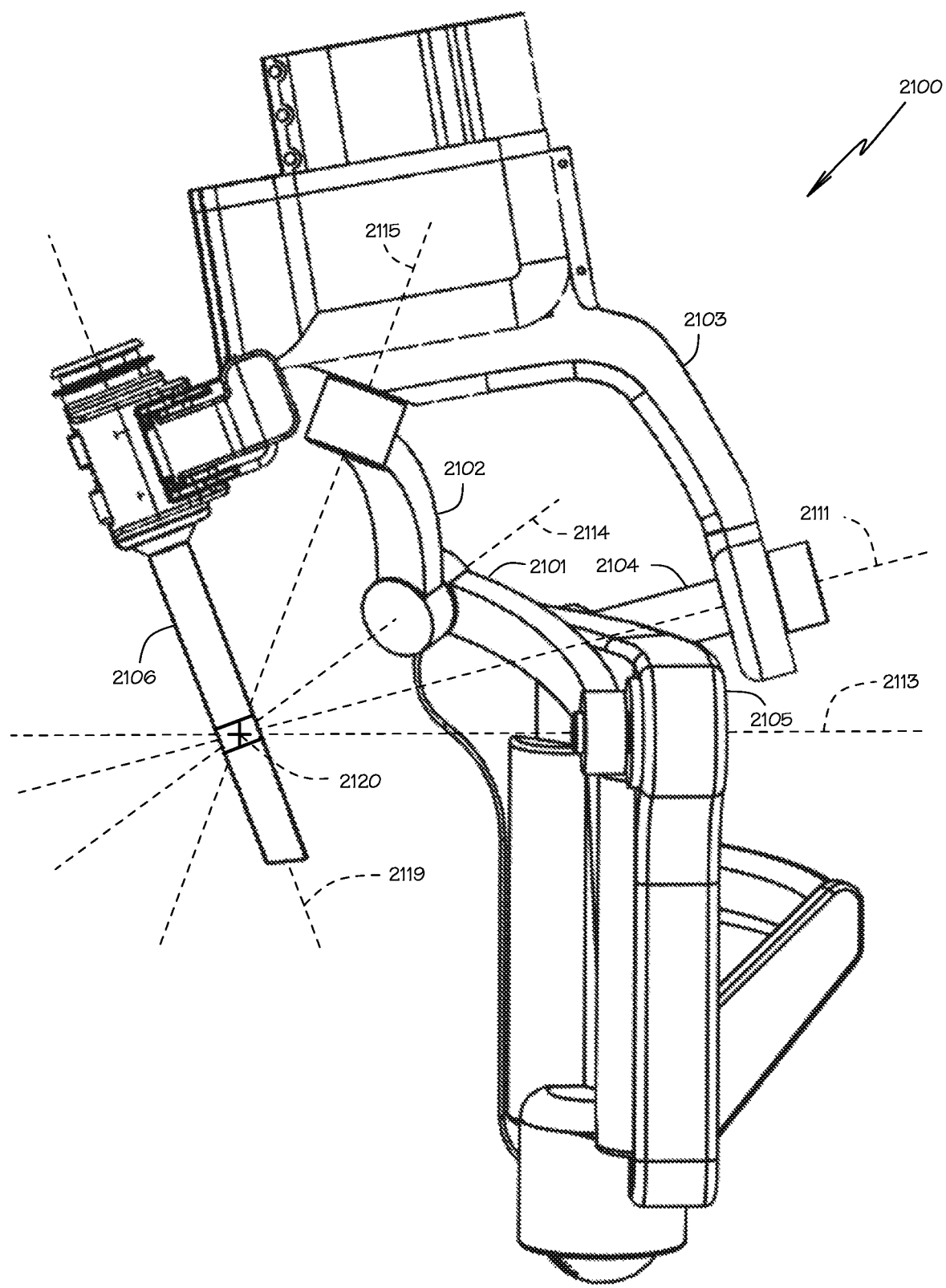
FIG. 21 is a pictorial view of another embodiment of the invention.

FIG. 21 shows another embodiment of a parallel spherical five-bar linkage 2100 for a robotic arm including two inboard links 2101, 2104, two outboard links, and a ground link provided by the motor assembly 2105. In comparison with the linkage 1900 of FIG. 19, the parallel spherical five-bar linkage 2100 includes an outboard link 2103 having an insertion axis 2119 that is spaced apart from the outboard axis 2115 by an offset distance. Ideally the insertion axis 2119 is coincident with the outboard axis 2115. Mechanical packaging advantages can be obtained, however, by separating the insertion axis 2119 from the outboard axis 2115.

Preferably the insertion axis 2119 will be placed on the outboard link 2103 further from the intermediate axis 2111 than the outboard axis 2115. As long as the insertion axis 2119 is perpendicular to the surface of the sphere centered on the remote center of spherical rotation 2120 and therefore passes through the remote center of spherical rotation 2120, then the insertion axis will have the same kinematic characteristics as the pivot axes 2111-2115 of the parallel spherical five-bar linkage 2100. That is, the insertion axis 2119 will move relative to the remote center of spherical rotation 2120. The insertion axis 2119 may or may not lie in the plane defined by the intermediate axis 2114 and the outboard axis 2115.

The placement of the insertion axis 2119 outboard from the pivot axes of the parallel spherical five-bar linkage may allow the endoscopic camera (not shown) to be supported and manipulated without interfering with the motion of the linkage 2100. It may also simplify the construction, installation, removal, and sterile boundary construction of the cannula 2106 and its associated mechanical attachment means.

In some embodiments having a spaced apart insertion axis, such as the one illustrated in FIG. 21, the insertion axis 2119, the outboard axis 2115, and the intermediate axis 2111 may be coplanar. This arrangement may simplify the relationship between the positions of the two inboard links 2101, 2104 and the position of the outboard axis 2115. Note that the insertion axis 2119 can be placed on either of the two outboard links 2102, 2103.

The parallel spherical five-bar linkage of the invention may be described using spherical geometry, which is a plane geometry on the surface of a sphere. While the links of the inventive linkage need not lie of the same spherical surface, or any spherical surface, they can be projected onto a common spherical surface for the purpose of describing the linkage. In spherical geometry, distances may be measured as angles because the geometric relationships on the spherical surface are unaffected by changing the radius of the sphere. Angular distance remains the same regardless of the radius of the sphere.

Navigation on the surface of the Earth is a common example of spherical geometry. Latitude and longitude as used in global navigation are a familiar system for describing locations and directions in a spherical system. The equator defines the points at 0° latitude. The north pole defines 90° latitude and the south pole defines −90° latitude. Longitude is the angular distance on a circle of constant latitude from an arbitrarily defined line of 0° longitude. Longitude is conventionally expressed as being in the range 180° west to 180° east of the 0° longitude line. Bearings are lines of direction from a point expressed as the angle between the bearing and a line of direction to the north pole. Westerly bearings can be expressed as positive angles and easterly bearings can be expressed as negative angles. The following is a description of an embodiment of the invention expressed in terms of a spherical geometry.

Referring again to FIG. 6, the first axis of rotation 613 of the first inboard link 601 will be considered as being at 0° latitude and 0° longitude. The second axis of rotation 612 of the second inboard link 604 is shown as being at the same latitude and at a positive (easterly) longitude. The second axis of rotation 612 may be at a fixed position of 55° longitude and 0° latitude, for example. Thus, in this example the ground link has an angular length of 55°. It should be remembered that a fixed position means fixed within the frame of reference of the spherical geometry of the linkage and that the entire linkage with its frame of reference may be freely positioned in space.

All of the movable links 601-604 may have the same angular length as the ground link. For example, the first intermediate axis 614 may be spaced apart from the first axis of rotation 613 by 55°. The first outboard axis 615 may be spaced apart from the first intermediate axis 614 by 55°. The insertion axis 619 may be spaced apart from the outboard axis 615 by 30°. The second intermediate axis 611 may be spaced apart from the second axis of rotation 612 by 55°. The second intermediate axis 611 may be spaced apart from the outboard axis 615 by 55°.

The range of rotation of the inboard links 601, 604 about the axes of rotation 613, 612 may constrained such that a minimum angle of 15° is maintained between the outboard links 602, 603, for example. The range of rotation of the inboard links 601, 604 may further constrained such that when the outboard axis 615 has a longitude of 27.5°, for example, the first inboard link 601 has a negative (easterly) bearing and the second inboard link 604 has a positive (westerly) bearing. The line segment that most directly connects the axis of rotation 613, 612 to the intermediate axis 614, 611 on the common spherical surface will cross the longitude line of the outboard axis 615 for both of the inboard links. Thus, the inboard links will cross one another when the outboard axis is at or near the center of its east-west range of motion. The constraints on the rotation of the inboard links prevents them from uncrossing when the outboard axis is in the central portion of its east-west range of motion.

These dimension are merely by way of example. The invention may be practiced with linkages having substantially different dimensions and substantially different ranges of motion. The invention is only limited by the claims. It may be desirable to use different dimensions and different ranges of motion to adapt the invention for needs of particular types of surgeries which have particular requirements for the range of motion of the insertion axis and for the space occupied by the device through its range of motion.

It is to be understood that the inventive parallel spherical five-bar linkage may be embodied in both powered and unpowered configurations. In powered embodiments, devices such as servo motors rotate the inboard links. The parallel spherical five-bar linkage translates those rotations into two dimensional movement of the outboard axis. In unpowered embodiments, two dimensional movement of the outboard axis is translated by the parallel spherical five-bar linkage into rotations of the inboard links. Devices such as rotary encoders may sense the bearings of the inboard links and that information may be used to compute the position of the outboard axis. Constraining the rotation of an intermediate axis as previously described is advantageous in unpowered embodiments because the constraint limits the position of the outboard axis to one of the two possible positions that correspond to the bearings of the inboard links.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Instead, the embodiments of the invention should be construed according to the claims that follow below.

What is claimed is:

1. A method for posing a robotic arm including a parallel spherical five-bar linkage in a minimally invasive surgical system, the method comprising:
   pivotally coupling each of two inboard links to opposing ends of a ground link;
   pivotally coupling two outboard links respectively to the two inboard links;
   pivotally coupling two outboard links together at an outboard axis;
   rotating the two inboard links to cross over one another.

2. The method of claim 1, further comprising supporting an endoscopic camera by at least one of the two outboard links.

3. The method of claim 1, further comprising:
   rotating a first one of the two inboard links with a first motor;
   rotating a second one of the two inboard links with a second motor; and
   controlling the first and second motors to pose the five-bar spherical linkage in only the range of compact poses in which the two inboard links cross over one another.

4. The method of claim 1, further comprising coupling a mechanical stop to the two outboard links to maintain a minimum angle of fifteen degrees between them.

5. The method of claim 1, further comprising coupling the ground link to a table to support the robotic arm over a patient.

6. The method of claim 1, further comprising coupling the ground link to a set-up arm to support the robotic arm over a patient.

7. A method for posing a robotic arm that includes a parallel five-bar spherical linkage to spherically rotationally move an endoscopic camera coupled to the parallel five-bar spherical linkage about a remote center of spherical rotation in a minimally invasive surgical system, the method comprising:

pivotally coupling a first inboard link and a first outboard link in the five-bar spherical linkage at a first intermediate joint;

coupling the first inboard link to a first end of a ground link in the five-bar spherical linkage;

pivotally coupling a second inboard link and a second outboard link in the five-bar spherical linkage at a second intermediate joint;

coupling the second inboard link to a second end of the ground link;

pivotally coupling the first outboard link to the second outboard link to form an outboard joint; and posing the five-bar spherical linkage in a compact pose with the second inboard link crossing the first inboard link.

8. The method of claim 7, further comprising:

rotating the first inboard link to a first position; and rotating the second inboard link to a second position such that the second inboard link crosses the first inboard link.

9. The method of claim 7, further comprising:

fixing a first motor to the first end of the ground link;

coupling the first motor to the first inboard link;

rotating the first inboard link with the first motor to a first position;

fixing a second motor to the second end of the ground link;

coupling the second motor to the second inboard link; and rotating the second inboard link with the second motor such that the second inboard link crosses the first inboard link.

10. The method of claim 7, further comprising coupling the ground link to a table to support the robotic arm over a patient.

11. The method of claim 7, further comprising coupling the ground link to a table with a set-up arm to support the robotic arm over a patient.

12. The method of claim 7, further comprising supporting the endoscopic camera by at least one of the two outboard links.

13. The method of claim 7, further comprising coupling a mechanical stop to the first outboard link to maintain a minimum angle of fifteen degrees between the first outboard link and the second outboard link.

* * * * *